(12) United States Patent
DeCoster et al.

(10) Patent No.: US 6,288,274 B1
(45) Date of Patent: *Sep. 11, 2001

(54) METHODS AND DEVICES FOR CONTROLLING THE REACTION RATE AND/OR REACTIVITY OF HYDROCARBON TO AN INTERMEDIATE OXIDATION PRODUCT BY ADJUSTING THE OXIDANT CONSUMPTION RATE

(75) Inventors: David C. DeCoster, Buckley, WA (US); Eustathios Vassiliou, Newark, DE (US); Mark W. Dassel, Indianola, WA (US); Sharon M. Aldrich, Poulsbo, WA (US); Ader M. Rostami, Bainbridge Island, WA (US)

(73) Assignee: RPC Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/253,172

(22) Filed: Feb. 19, 1999

Related U.S. Application Data (63) Continuation of application No. PCT/US97/12944, filed on Jul. 23, 1997, application No. 08/861,281, filed on May 21, 1997, and application No. 08/859,985, filed on May 21, 1997.
(60) Provisional application No. 60/025,374, filed on Sep. 3, 1996, and provisional application No. 60/024,263, filed on Aug. 21, 1996.

(51) Int. Cl.[7] .................................................. C07C 51/31
(52) U.S. Cl. ........................................ 562/543; 562/542
(58) Field of Search .................................. 562/509, 542, 562/543, 590, 593; 502/504

(56) References Cited

U.S. PATENT DOCUMENTS

| | | |
|---|---|---|
| 1,121,532 | 12/1914 | Newberry . |
| 2,014,044 | 9/1935 | Haswell ................................... 75/17 |
| 2,223,493 | 12/1940 | Loder ................................... 260/537 |

(List continued on next page.)

FOREIGN PATENT DOCUMENTS

4426132 A1   1/1996   (DE) .

(List continued on next page.)

OTHER PUBLICATIONS

Lewis, *Hawley's Condensed Chemical Dictionary*, 12th ed., 1993, pp. 7, 336, and 1076.

(List continued on next page.)

*Primary Examiner*—Gary Geist
*Assistant Examiner*—Taylor Oh
(74) *Attorney, Agent, or Firm*—Seed Intellectual Property Law Group PLLC (57) ABSTRACT

Methods and devices for controlling the reaction rate and/or reactivity of a hydrocarbon to an intermediate oxidation product, such as an acid, within predetermined limits, are disclosed. Control of the reaction rate and/or reactivity within predetermined limits is achieved by monitoring and controlling the oxidant consumption rate. According to the present invention, examples of ways to determine the oxidant consumption rate include, but are not limited to, monitoring the flow rates of incoming and outgoing oxidant, monitoring pressure differentials after temporarily ceasing entry and exit of gases, and monitoring the flow rates of incoming and outgoing gases, and monitoring the rates of incoming and outgoing hydrocarbon. The methods and devices of the present invention are particularly advantageous in the case that the hydrocarbon is cyclohexane, the intermediate oxidation product is adipic acid, the solvent is acetic acid, the catalyst is cobalt (II) acetate tetrahydrate, and the initiator or promoter is cyclohexane, or acetaldehyde, or a mixture of thereof.

24 Claims, 3 Drawing Sheets

U.S. PATENT DOCUMENTS

| | | | |
|---|---|---|---|
| 2,223,494 | 12/1940 | Loder | 260/537 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,839,435 | 10/1974 | Shigeyasu et al. | 260/524 R |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,025,498 | 5/1977 | Buss et al. | 260/95 A |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,160,108 | 7/1979 | Shigeyasu et al. | 562/416 |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 R |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 4,603,220 | 7/1986 | Feld | 562/416 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,505,920 | 4/1996 | Kollar et al. | 423/246 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,801,273 | 9/1998 | Vassiliou et al. | 562/413 |
| 5,801,282 | 9/1998 | Dassel et al. | 562/413 |
| 6,103,933 * | 8/2000 | DeCoster et al. | 562/509 |

FOREIGN PATENT DOCUMENTS

| | | |
|---|---|---|
| 4427474 A1 | 2/1996 | (DE) . |
| 439 007 A2 | 7/1991 | (EP) . |
| 729 084 A1 | 8/1996 | (EP) . |
| 729 085 A1 | 8/1996 | (EP) . |
| 751 105 A2 | 1/1997 | (EP) . |
| 2 722 783 A1 | 1/1996 | (FR) . |
| 415172 | 8/1934 | (GB) . |
| 738808 | 10/1955 | (GB) . |
| 864106 | 3/1961 | (GB) . |
| 1143213 | 2/1969 | (GB) . |
| 2014473 A | 8/1979 | (GB) . |
| 48-003815 | 2/1973 | (JP) . |
| WO 96/03365 | 2/1996 | (WO) . |
| WO 96/40610 | 12/1996 | (WO) . |

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+ English language translation).

U.S. application No. 08/587,967, Mark W. Dassel and Eustathios Vassiliou, filed Jan. 17, 1996.

U.S. application No. 08/812,847, Mark W. Dassel, Eustathios Vassiliou, David C. DeCoster, Ader M. Rostami, and Sharon M. Aldrich, filed Mar. 6, 1997.

U.S. application No. 08/824,992, Mark W. Dassel, David C. DeCoster, Ader M. Rostami, Sharon M. Aldrich, and Eustathios Vassiliou, filed Mar. 27, 1997.

\* cited by examiner

METHODS AND DEVICES FOR CONTROLLING THE REACTION RATE AND/OR REACTIVITY OF HYDROCARBON TO AN INTERMEDIATE OXIDATION PRODUCT BY ADJUSTING THE OXIDANT CONSUMPTION RATE

CROSS-REFERENCE TO RELATED APPLICATION

This application is a continuation under 35 U.S.C. 111(a) of International Application PCT/US97/12944, with an international filing date of Jul. 23, 1997, now pending; which claims the benefit of U.S. application Ser. No. 08/861,281, filed May 21, 1997; U.S. application Ser. No. 08/859,985, filed May 21, 1997; U.S. Provisional Application No. 60/025,374, filed Sep. 3, 1996; and U.S. Provisional Application No. 60/024,263, filed Aug. 21, 1996; which applications are incorporated herein by reference in their entirety.

TECHNICAL FIELD

This invention relates to methods and devices for making intermediate oxidation products, and especially dibasic acids, by oxidizing a hydrocarbon under controlled conditions.

BACKGROUND OF THE INVENTION

There is a plethora of references (both patents and literature articles) dealing with the formation of intermediate oxidation products, such as for example acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and initiators or promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references. It is also important to note that most studies on the Direct Oxidation have been conducted in a batch mode, literally or for all practical purposes.

There is a plethora of references dealing with oxidation of organic compounds to produce acids, such as, for example, adipic acid and/or other intermediate oxidation products, such as for example cyclohexanone, cyclohexanol, cyclohexylhydroperoxide, etc.

The following references, among the plethora of others, may be considered as representative of oxidation processes relative to the preparation of diacids and other intermediate oxidation products.

U.S. Pat. No. 5,463,119 (Kollar), U.S. Pat. No. 5,374,767 (Drinkard et al.), U.S. Pat. No. 5,321,157 (Kollar), U.S. Pat. No. 3,987,100 (Barnette et al.), U.S. Pat. No. 3,957,876 (Rapoport et al.), U.S. Pat. No. 3,932,513 (Russell), U.S. Pat. No. 3,530,185 (Pugi), U.S. Pat. No. 3,515,751 (Oberster et al.), U.S. Pat. No. 3,361,806 (Lidov et al.), U.S. Pat. No. 3,234,271 (Barker et al.), U.S. Pat. No. 3,231,608 (Kollar), U.S. Pat. No. 3,161,603 (Leyshon et al.), U.S. Pat. No. 2,565,087 (Porter et al.), U.S. Pat. No. 2,557,282 (Hamblet et al.), U.S. Pat. No. 2,439,513 (Hamblet et al.), U.S. Pat. No. 2,223,494 (Loder et al.), U.S. Pat. No. 2,223,493 (Loder et al.), German Patent DE 44 26 132 A1 (Kysela et al.), and PCT International Publication WO 96/03365 (Constantini et al.).

None of the above references, or any other references known to the inventors disclose, suggest or imply, singly or in combination, oxidation reactions to intermediate oxidation products under conditions subject to the intricate and critical controls and requirements of the instant invention as described and claimed.

Our U.S. Pat. Nos. 5,580,531, 5,558,842, 5,502,245, as well as our PCT International Publication WO 96/40610 describe methods and devices relative to controlling reactions in atomized liquids.

SUMMARY OF THE INVENTION

As aforementioned, this invention relates to methods and devices for making intermediate oxidation products, and especially dibasic acids, by oxidizing a hydrocarbon under controlled conditions. More particularly, it relates to a method of controlling the oxidation of a hydrocarbon to an intermediate oxidation product in a reaction zone, the method characterized by the steps of:

(a) contacting a gas comprising oxidant with a hydrocarbon by feeding the gas at a first flow rate, and the hydrocarbon into the reaction zone, at a first pressure, and at a first temperature adequately high to allow the oxidant to react with the hydrocarbon at a reaction rate and/or reactivity; and (b) controlling consumption rate of the oxidant in a manner that the reaction rate and/or the reactivity is maintained within predetermined limits.

The consumption rate of the oxidant is defined as the amount of oxidant (preferably in weight units) consumed per unit of time.

According to this invention, reaction rate is defined as the molar oxidation of hydrocarbon per unit of time, and the reactivity is defined as the reaction rate divided by the total volume of non-gaseous mixture involved in the reaction. Also, according to this invention, reference to controlling or maintaining the reaction rate or the reactivity within a desired range, includes the case of controlling and/or maintaining both the reaction rate and the reactivity within desired ranges.

An intermediate oxidation product is defined as an oxidation product of a hydrocarbon, which is different than carbon monoxide or carbon dioxide.

The reaction rate may be determined very accurately, in a continuous reactor for example, by subtracting the amount of hydrocarbon exiting the system per unit of time from the hydrocarbon entering the system per unit of time. Depending on the configuration of a reactor system or device, amounts of hydrocarbon entering or exiting the system per unit time may be either known facts or facts, or may be determined by chemical analysis and stream flow rate data, or may be a combination of both. This type of information may be easily processed by a controller so that a predetermined program may be followed, as explained in detail hereinbelow.

The oxidant consumption rate may be arbitrarily considered as a variable proportional to the reaction rate, and/or as a variable proportional to pressure drop rates or proportional to differences of incoming and outgoing gas flows, or proportional to differences of incoming and outgoing oxidant flows, or proportional to differences of incoming and outgoing hydrocarbon flows, as described below.

In one embodiment of this invention, the consumption rate of the oxidant is determined by the difference of oxidant entering the reaction zone and oxidant leaving the reaction zone per unit of time. The consumption rate of the oxidant may also be indirectly determined by the difference of hydrocarbon entering the reaction zone and hydrocarbon leaving the reaction zone per unit of time.

It is evident that in all cases, matter recycled to the reaction zone has to be taken into account for determining consumption rates, reaction rates, reactivity, etc.

In another embodiment, the consumption rate of the oxidant is determined by conducting at least one step of the following, after stopping gas feed into the reaction zone and after stopping the removal of non-condensible off-gases from the reaction zone:

(i) determining the time it takes for the oxidant contained in the reaction zone to cause a reaction in a manner that the reaction zone attains a predetermined second pressure, lower than the first pressure; and (ii) allowing the oxidant to cause a reaction, and measuring the pressure drop within a predetermined interval of time.

It is important that the oxidant is allowed to continue reacting, for example by being brought in contact with the hydrocarbon.

In still another embodiment, the consumption rate of the gaseous oxidant is determined by the difference between the first flow rate (flow rate of the incoming gases) and the flow rate of non-condensible off-gases.

The consumption rate of the oxidant may be controlled by regulating a variable selected from a group consisting of temperature, pressure, partial pressure of oxidant, flow rate of oxidant, sparging rate, recycled gas flow rate, flow rate of hydrocarbon, flow rate of solvent, flow rate of catalyst, flow rate of water, flow rate of initiator or promoter, and a combination thereof. Flow rates of the miscellaneous components determine the concentration of said components in the reaction zone, for all practical purposes. Thus, the consumption rate of the oxidant may also be controlled by determining and appropriately altering the concentration of the different components in the reaction zone.

The method may comprise a step of atomization of liquids entering the reaction zone.

The methods of the present invention are particularly beneficial in the case that the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

The present invention further pertains a device for controlling the oxidation of a hydrocarbon to an intermediate oxidation product at a reaction rate, the device characterized by:

a reaction chamber;

oxidant feeding means, connected to the reaction chamber, for feeding predetermined amounts or rates of a gas comprising oxidant into the reaction chamber;

hydrocarbon feeding means, connected to the reaction chamber, for feeding a predetermined amount or rate of a hydrocarbon into the reaction chamber;

oxidant consumption determining means, connected to the reaction chamber, for determining the rate of oxidant consumption in the reaction chamber; and oxidant consumption control means, connected to the reaction chamber, for controlling the rate of oxidant consumption in the reaction chamber in a manner to maintain the reaction rate or the reactivity within predetermined limits.

The device preferably comprises a controller connected to the oxidant consumption determining means and to the oxidant consumption control means, the controller being programmed to obtain information from the oxidant consumption determining means and use this information to influence the oxidant consumption control means to be varied in a manner to cause the reaction rate or the reactivity to be maintained within the predetermined limits.

The device may further comprise oxidant inlet monitoring means for determining the flow rate of oxidant entering the reaction chamber, and oxidant outlet monitoring means for determining the flow rate of oxidant exiting the reaction chamber, both monitoring means being connected to the controller, directly or indirectly, for providing inlet and outlet flow information to the controller, the information being used for determining the rate of consumption of oxidant.

It is important that recycled condensible and non-condensible matter flow into the reaction zone is taken into account for the miscellaneous determinations.

The device may comprise:

interrupting means for stopping temporarily in predetermined intervals entering of gases into the reaction chamber and exiting of gases from the reaction chamber; and wherein the oxidant consumption determining means comprise a pressure monitor for measuring the pressure inside the reaction chamber, and for providing pressure differential information to the controller, during the temporary stopping of entering and exiting gases, for determining the rate of oxidant consumption.

The oxidant consumption determining means may comprise gas entering means and non-condensible off-gas exiting means for determining the difference between flow of gas entering the reaction chamber and flow of non-condensible gas exiting the reaction chamber, respectively, and determining the oxidant consumption rate from the difference of the flows.

The reactor devices of the present invention may further comprise one or more of:

temperature monitoring means for monitoring the temperature in the reaction chamber;

pressure monitoring means for monitoring the pressure in the reaction chamber;

solvent feeding means connected to the reaction chamber for feeding a predetermined amount or rate of a solvent into said reaction chamber;

catalyst feeding means connected to the reaction chamber for feeding a predetermined amount or rate of a catalyst into said reaction chamber;

initiator or promoter feeding means connected to the reaction chamber for feeding a predetermined amount or rate of a promoter into said reaction chamber;

water feeding means connected to the reaction chamber for feeding water into the reaction chamber; and recycle feeding means connected to the reaction chamber for recycling matter to the reaction chamber.

The controller may be connected to at least one of the temperature monitoring means, the pressure monitoring means, the oxidant feeding means, the hydrocarbon feeding means, the solvent feeding means, the catalyst feeding means, the recycle feeding means, and the initiator or promoter feeding means; the controller being programmed to adjust at least one of said temperature monitoring means, oxidant feeding means, hydrocarbon feeding means, solvent feeding means, catalyst feeding means, the water feeding means, and initiator or promoter feeding means, in a manner to either give an indication to an operator, if the reaction rate or the reactivity is found to be outside the predetermined ranges, or to adjust the oxidant consumption rate so as to bring back and maintain said reaction rate or said reactivity, respectively, within said desired ranges.

Two or more of the oxidant feeding means, hydrocarbon feeding means, solvent feeding means, catalyst feeding means, and promoter feeding means may be combined to one combination means.

The reaction chamber may be at least part of an atomization, or at least part of a stirred-tank reactor, or any other type of reactor.

BRIEF DESCRIPTION OF THE DRAWINGS

The reader's understanding of this invention will be enhanced by reference to the following detailed description taken in combination with the drawing figures, wherein.

DETAILED DESCRIPTION OF THE INVENTION

As mentioned earlier, this invention relates to methods of making intermediate oxidation products, such as acids, for example, by oxidizing a hydrocarbon with a gas containing an oxidant, preferably oxygen.

The reaction rate and the reactivity in an oxidation, such as for example the direct oxidation of cyclohexane to adipic acid, is very important for a number of reasons, among which productivity is of major significance. High productivity may be also compromised with lower temperatures, which usually result in better selectivity and yield. Since in a process, productivity has usually to be compromised with selectivity and yield, a predetermined optimal solution has to be found, depending on each particular occasion. Thus, control of the reaction rate, and more importantly reactivity, during an oxidation is of utmost importance.

According to a preferred embodiment of this invention, pressure drop rate monitoring and control, achieves a fast and easy way to control the oxidant consumption rate, and in turn maintain the reaction rate and the reactivity within desirable predetermined limits.

To measure the pressure drop rate, a number of different techniques may be used, among which the most preferred ones are:

after the reaction chamber is pressurized, the feeding and exiting of gases is stopped temporarily, and the time for the initial pressure (first pressure) to drop to a second predetermined pressure level is measured; and after the reaction chamber is pressurized to a first pressure, the feeding and exiting of gases is stopped and a second pressure attained in a predetermined period of time is measured.

The above measurements and operations may be made in a continuous basis, or a sporadic basis, or in any desirable predetermined pattern.

It is preferable, especially in the case of stirred-tank reactors, that large amounts of non-condensible gases are recirculated, in order to avoid pressure changes due to reasons irrelevant to the consumption of oxidant.

During the pressure measurements, the reaction has to continue taking place, and therefore the liquids in the reaction chamber have to continue being in close contact with the oxidant. In the case of a stirred-tank reactor, sparging of gases for example comprising the oxidant should continue, preferably by recirculation. In the case of an atomization reactor, recirculation of the atomized liquids into the reaction zone for example should also continue.

Figure 1:
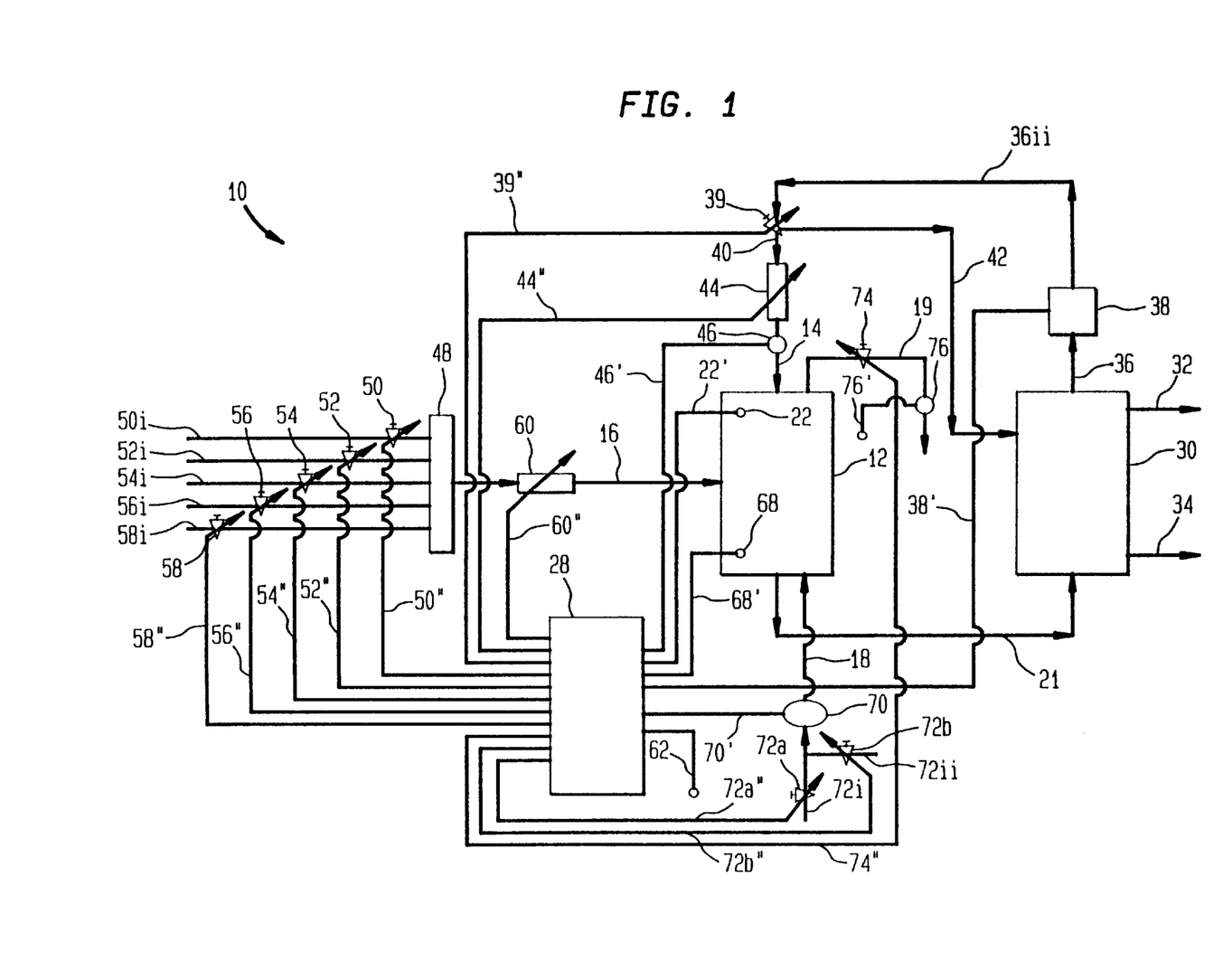
FIG. 1 illustrates schematically a reactor device which may be used in the practice of preferred embodiments of the present invention.

A preferred embodiment of this invention is illustrated in FIG. 1. In FIG. 1, there is depicted a device or continuous reactor system 10 comprising a reaction chamber 12. The reaction chamber 12 may be any type of reaction chamber, according to the instant invention. Examples of reaction chambers are atomization reactors as described for example in our U.S. Pat. Nos. 5,502,245, 5,580,531, 5,558,842, stirred tank reactors, recirculation reactors (in which the stirring is conducted by recirculation, and they are included in the stirred tank reactor category as far as this invention is concerned), and the like. A recycle feeding or inlet line 14, a new raw material feeding or inlet line 16, a gaseous oxidant feeding or inlet line 18, a gas outlet line 19, a predominantly non-gaseous outlet line 21, a monitor for measuring temperature, such as thermocouple 22 for example, and means for measuring pressure, such as gauge or transducer 68 for example, are connected to the reaction chamber 12. Inlet line 18 is fed by merging lines 72i and 72ii through flowmeter 70 and valves 72a and 72b, which valves are controlled by the controller 28, through output lines 72a" and 72b", respectively. In line 19, there are disposed valve 74 and flowmeter 76. Flowmeter 76 is connected to the controller 28 through input line 76'(not shown connected for purposes of clarity) to give gas flow information to said controller 28. The controller 28 controls valve 74 through output line 74".

Other elements, commonly used with reaction chambers, such as condensers, decanters, distillation columns, recycle gas means, and the like, for example, in line 19 before or after the valve 74 or flowmeter 76, are not shown in FIG. 1 for purposes of clarity. Also, optional means for conducting chemical analysis of the contents of the reaction chamber 12 are not shown, also for purposes of clarity. The optional means (not shown) for conducting chemical analysis of the contents of the reaction chamber 12, preferably, also provide ingredient content information to the controller 28. The inlet, outlet, input or output lines may be positioned in any suitable location of the reaction chamber 12. The words "inlet" and "outlet" are used for lines which feed or withdraw materials, respectively, while the words "input" and "output" are used for lines which provide information to the controller 28, or are utilized by the controller to control other elements of the device, respectively.

The predominantly non-gas outlet line 21 leads to a material management station 30, at which the products of reaction, any by-products, non-converted raw materials, etc., are separated by well known to the art techniques. Such techniques may involve filtration, distillation, crystallization, other types of separation, evaporation, cooling, heating, storage, decontamination, incineration, disposal, etc.

The desired product of reaction follows product path 32, the non-recyclable by-products follow non-recyclables path 34, while recyclable materials follow recyclables line 36, which line 36 leads to an analytical apparatus 38 for analysis of the contents of the recyclables. The analytical apparatus 38 samples and analyzes the recyclables before they enter line 36ii. Line 36 may comprise one or a plurality of lines, depending of the nature of the recyclables. Some of these lines may even circumvent the analytical apparatus 38, if so desired (if for example the content of the recyclable material under consideration is known or previously determined by any of well known to the art techniques).

The recyclables follow line 36ii, which leads to a three way valve 39, in a manner that the recyclables may follow line 40 or 42 or both in any desired ratio. Line 42 leads back to the material management station 30 for storage or retention or re-work, or the like, while line 40 leads to a first heat exchanger (including cooler or heater or the like) 44.

The 3 way valve 39 is controlled by the controller 28 through output line 39". Similarly, the heat exchanger 44 is controlled by the controller 28 through output line 44". Preferably one or more input lines (not shown for purposes of clarity) provide temperature information to the controller 28 regarding the recyclables as they enter and exit the heat exchanger 44.

The recyclables enter the reaction chamber 12 after they pass through flowmeter 46, which gives recyclables flow data to the controller 28 through input line 46'.

Input lines 22' and 68' feed the controller 28 with temperature information and pressure information, respectively, within the reaction chamber 28. More lines may be necessary, depending on the information required in each particular case.

Flow regulation valves 50, 52, 54, 56, and 58 are connected to inlet lines 50i, 52i, 54i, 56i, and 58i, which provide hydrocarbon, solvent, catalyst, promoter, and other adjuncts, respectively, to a pre-mixing vessel 48. The premixing vessel 48 is preferably of small size and positioned in a way that all its contents are moving out of it and through line 16, so that if more than one phase is present, there is no accumulation of a particular phase in the pre-mixing vessel. Pre-mixing vessel 48 is connected with a second heat exchanger (including cooler or heater or the like) 60, which in turn is connected to the reaction chamber 12. The inlet lines 50i, 52i, 54i, 56i, and 58i, may however be directly connected to the second heat exchanger 60 or to the reaction chamber 12.

The inlet lines 50i, 52i, 54i, 56i, and 58i may be heated or cooled separately with their own individual heaters or coolers (not shown for purposes of clarity), which heaters or coolers are preferably controlled by controller 28. With this arrangement, formation of two phases may be avoided in premixing vessel 48. The heat exchanger 60 may then be omitted or it may be used for fine tuning of the final temperature.

Flow regulation valves 50, 52, 54, 56, and 58 are controlled by the controller 28 through output lines 50", 52", 54", 56", and 58", respectively. A number of flowmeters (not shown for purposes of clarity) connected to lines 50i, 52i, 54i, 56i, and 58i, provide flow information regarding hydrocarbon, solvent, catalyst, promoter, and other adjuncts, to the controller 28 through multiple input line 62.

The reaction chamber 12 may be heated or cooled by heating or cooling means (not shown) well known to the art.

The lines 14 and 16 may merge together into a single line (not shown), and feed the reaction chamber through said single line.

In operation of this embodiment, hydrocarbon, solvent, catalyst, initiator or promoter and any other desired adjuncts are added to the pre-mixing vessel 48, where they are mixed together. The pre-mixing vessel is small enough and positioned in a manner that if there is phase separation, no particular phase remains behind, but all phases are commingled and they proceed through the second heat exchanger 60 and to the reaction chamber 12 through line 16. The feed rates of the new raw materials fed through lines 50i, 52i, 54i, 56i, and 58i depend on the feed rates of the recyclables fed to the reaction chamber 12 through recycle feeding line 14. Information regarding the analytical results from the analytical apparatus 38 is provided to the controller 28, which combines this information with the information from the flowmeter 46 and the information from the flowmeters (not shown) of lines 50i, 52i, 54i, 56i, and 58i, and calculates the total feed rate of each individual ingredient entering the reaction chamber 12.

The controller preferably gives precedence to the recyclables, and then it adjusts each of the valves 50, 52, 54, 56, and 58 through output lines 50", 52", 54", 56", and 58", respectively, in a manner that the total feed rate of each individual ingredient entering the reaction chamber 12 has a desired value. The desired value of each ingredient feed rate is preferably adjusted toward a desired range of values of pressure drop, as will be discussed later.

Of course, when the operation starts, there are no recyclable materials, so that only new raw materials start entering the system through one or more of lines 50i, 52i, 54i, 56i, and 58i, and finally enter the reaction chamber 12 through line 16. During starting the operation, the different feed rates of new raw materials are arranged so that the pressure drop rate falls within the predetermined range. An initiation period, before the reaction starts, has to be taken into account. Preferably, the reaction is driven toward formation of a single phase.

The balance of materials is also preferably arranged to be such that when water starts being formed during the oxidation, no second phase is formed. Second phase formation leads to considerably reduced reactivity. This, however, is not necessary, albeit highly preferable, for the practice of the instant invention. The amount of water formed depends on the conversion taking place when the system attains a steady state. The more solvent, acetic acid for example, that is present at this steady state, the more water may be withstood by the system without formation of a second phase. Since the formation of water is substantially unavoidable when a hydrocarbon is oxidized, and in some respects its presence may even be desirable (for at least partial hydrolysis of undesirable ester by-products, for example), it is preferable to work at a steady state which can contain at least a predetermined content of water without the formation of a second phase. Removal of water in any step of the process, if necessary or desired, may be achieved by a number of ways, including for example distillation, addition of acid anhydrides, and other well known to the art methods.

The more hydrocarbon, cyclohexane for example, that is present in the reaction chamber the higher the potential for formation of a second phase. At the same time, if too little hydrocarbon is present, the reaction starts starving from lack of hydrocarbon. According to the instant invention, the amount of hydrocarbon present in the steady state is preferably just above the point at which starvation is observed. "Just above" starvation means preferably between 0 to 20% above starvation, and more preferably 5 to 20% above starvation.

At the same time that the above mentioned ingredients enter the reaction chamber 12, a gas containing an oxidant, preferably oxygen, enters the reaction chamber through the gaseous oxidant feeding line 18, and it comes in contact with the mixture containing the hydrocarbon. Oxidant, or gas comprising oxidant, may be recirculated in the system for better sparging, especially in the case of stirred-tank reactors. It is preferable that the oxidant, or gas comprising oxidant, for recirculation is obtained at a point before valve 74 (between valve 74 and the reaction chamber 12), as it is described at a later point.

The reaction temperature or first temperature is monitored by one or more thermocouples, such as thermocouples 22 for example, which provide temperature information to the controller 28. The pressure in the reaction chamber 12 is monitored by the pressure gauge or transducer 68, which provides pressure information to the controller 28 through input line 68'.

The controller 28, based on this temperature information adjusts the first and second heat exchangers through output lines 44" and 60", respectively, in a manner that in combination with the heat released by the reaction, and the thermal characteristics of the reaction chamber 12, the temperature attains and maintains a desired value. In order to lower the temperature in the reaction chamber, the heat exchangers are adjusted to lower the temperatures in lines 14 and 16. In addition to or instead of this, the reaction chamber itself may be provided with heating and/or cooling means (not shown for purposes of clarity, but well known to the art), controlled by the controller 28, so that the temperature attains and maintains the desired value. The desired value may, of course, be a desired range of values.

Alternately, the controller 28, based on this pressure information, may adjust the reaction chamber pressure using valve 74, which will establish a new thermal equilibrium in the reaction chamber 12 at a new temperature.

When the temperature is raised, the potential for maintenance or formation of a single liquid phase is increased, and the rate of reaction is increased. However, the selectivity to the desired final product may suffer. Therefore, a balance among rate of reaction, selectivity, and temperature has to be decided. This decision may depend on the particular circumstances, and may be based on economical, safety, environmental, and other considerations.

Thus, the temperature may preferably be adjusted through the controller 28 within the desired range in a manner to promote the formation and/or maintenance of a single phase. If a single phase already exists, the temperature may preferably be reduced to the minimum limit of the desired range, and maintained there, if this decrease in temperature does not cause the formation of a second phase.

For constant purge rates of non-condensibles from the reaction chamber 12, lowering the pressure within the reaction chamber 12 moves the system toward a single phase formation since more hydrocarbon, cyclohexane for example, evaporates and the content of hydrocarbon in the liquid decreases.

Increasing gas sparging in the case of a stirred-tank reaction chamber, or in general the flow of the gaseous oxidant in the case of an atomization reactor (described for example in our aforementioned patents) has a similar effect as lowering the pressure.

Lowering the conversion, or hold-up time in the reaction chamber 12, decreases the amount of water formed, which decrease has as an effect to promote the formation of a single phase.

Lowering the amount or flow rate of catalyst, cobalt-comprising catalyst for example, in the reaction chamber 12, also promotes the maintenance or formation of a single liquid phase. It should be noted here that when cobaltous acetate tetrahydrate is used, water is necessarily introduced, corresponding to the water of hydration of the cobaltous acetate salt.

According to the instant invention, the pressure is monitored by the pressure monitor 68, and the information is fed to the controller 28 through input line 68'.

A gas comprising oxidant, preferably oxygen enters the system through line 18, which line 18 is fed from lines 72$i$ and 72$ii$, which in turn comprise valves 72$a$ and 72$b$, respectively. Valves 72$a'$ and 72$b'$ are controlled by the controller 28 through output lines 72$a''$ and 72$b''$, respectively. Although it is preferable for the line 18 to be fed by the two lines 72$i$ and 72$ii$, it may also be fed by just one of the two lines, as long as that one line comprises oxidant, preferably oxygen. In the particular case of this example, line 72$i$, conducts a gas containing oxidant, such as air for example, and line 72$ii$ conducts oxidant, such as oxygen for example. The exact content of oxidant in the lines may assume any values, as long as a controlled amount or rate of oxidant may be fed to line 18. It is preferred that line 72$i$ conducts air or an inert gas, such as nitrogen for example, and line 72$ii$ conducts oxygen.

When the pressure inside the reaction chamber reaches a desired first pressure value, the valves 72$a$, 72$b$ and 74 are caused to close by the controller 28, and the first pressure is allowed to drop to a second pressure value, preferably close to the first pressure value. The time interval between the two pressures determines the pressure drop rate. Alternatively, the pressure drop rate may be determined by measuring the first pressure and the pressure attained within a predetermined time interval. The time interval is preferably in the range of $1/5$ to $1/100$ of the hold up time in the reaction chamber, and more preferably in the range of $1/5$ to $1/50$ of the hold up time in the reaction chamber.

As aforementioned, during the pressure measurements, the reaction has to continue taking place, and therefore the liquids in the reaction chamber have to continue being in close contact with the oxidant. In the case of a stirred-tank reactor, sparging of gases for example comprising the oxidant should continue, preferably by recirculation. In the case of an atomization reactor, recirculation of the atomized liquids into the reaction zone for example should also continue.

The determination of the pressure drop rate is very important because it is a measure of the reaction rate. In turn, the reaction rate is important because of higher reactivity and productivity. Also with higher rates, lower temperatures may be utilized, which in turn may result in better selectivity and yield. Of course, a balance should be selected and exercised between selectivity/yield, and reaction rate or reactivity.

Carbon dioxide and carbon monoxide monitors (not shown) in the non-condensible off-gases are also preferably utilized because they are indicative of selectivity and yield. An oxygen monitor 92 (shown in FIG. 2) is also used for determination of the oxygen content in the non-condensible off-gases, according to another preferred embodiment of the present invention. Of course, the oxidant content may be determined at an earlier stage, such as between the reaction chamber 12 and the condenser 84 for example.

When the determination of pressure drop rate is completed, valve 72$b$ is controllably opened for the missing oxidant, preferably oxygen, to enter the reaction chamber, and raise the pressure to attain its first pressure value again. When the first pressure value has been achieved in the reaction chamber 14, valves 72a and 74 also are controllably opened in a manner to maintain the first pressure value in the reaction chamber 12. Measurements of flow through the flowmeters 70 and 76 are useful for information to be sent to the controller 28, which adjusts in turn valves 72a, 72b and 74 appropriately.

In place or in addition to flowmeter 70, flowmeters (not shown) in both or one of lines 72i and 72ii may be used for more information.

Instead of the sequence of valve openings and closings described above any other sequence may be utilized as long as the pressure drop rate due to oxidant, preferably oxygen, consumption is measured.

When the determination of pressure drop rate has been made by the controller 28, which is a measure of the oxidant consumption rate, action is taken to control said pressure drop rate, and in a parallel manner the reaction rate or the reactivity, to fall within desired ranges or limits.

If the measured pressure drop rate, which is a measure of the oxidant consumption rate, and in turn of the reaction rate, is less than the desired range of values, the controller is for example preferably programmed to follow the following sequence of steps to raise the pressure drop rate. However, depending on the individual circumstances, the sequence may be changed, a number of steps may be omitted, or other steps added. If a step is proven to be ineffective during the operation, any action that was taken to perform the step may be reversed and the next step conducted. Preferably, small increases or decreases of feed rates or other parameters are conducted to avoid overshooting. These depend on the individual case, and they may be easily determined by a person of ordinary skill in the art:

the partial pressure of oxidant, preferably oxygen, may be increased by controlling valves 72a and 72b in a manner for example that the valve 72b provides more oxidant; although the total pressure within the reaction chamber 12 is preferably constant, except for the fluctuations needed to measure the pressure drop rate, the total pressure may be increased in a manner that the partial pressure of oxidant is also increased; this is especially useful in case that the two valves 72a and 72b are replaced with a single valve providing line 18 with a mixture of oxidant and inert gas of a constant composition;

the feed rate of hydrocarbon, preferably cyclohexane in the case of production of adipic acid, is increased, especially when the operation takes place close to the limit under which hydrocarbon starvation may be the cause of decrease of the pressure drop rate; this may be arranged by controller 28 through output line 50" which controls valve 50;

the feed rate of catalyst, preferably comprising cobalt ions, is increased through valve 54, which is controlled by the controller 28 through output line 54";

the feed rate of initiator or promoter is increased through valve 56, which is controlled by the controller 28 through output line 56";

the feed rate of solvent is initially increased through valve 52, which is controlled by the controller 28 through output line 52"; if this has no effect or negative effect, the feed rate of solvent is decreased from its initial value and the effect is also evaluated; if a beneficial effect is achieved, the feed rate of solvent is further decreased within predetermined limits, and so on;

the temperature in the reaction chamber 12 is increased either by means of one or both heat exchangers 44 and 60 through lines 44" and 60", respectively, or by adding more heat directly to the reaction chamber, or removing less heat directly from the reaction chamber, or decreasing the sparging rate of non-condensible gases, such as nitrogen for example, to the reaction chamber, or by increasing the reaction pressure so as to decrease the volatilization of condensible matter.

The opposite procedures may be followed if the pressure drop rate is too high. The controller 28 also compares analytical results of the reaction products, preferably from line 21, and from the aforementioned gas monitors (CO, $CO_2$ and $O_2$) with the influence of the above steps on pressure drop rate, yield, selectivity, conversion, and the like, and optimizes the process according to a predetermined desirable program, depending on the individual occasion, readily designed by a person of ordinary skill in the art.

Figure 3:
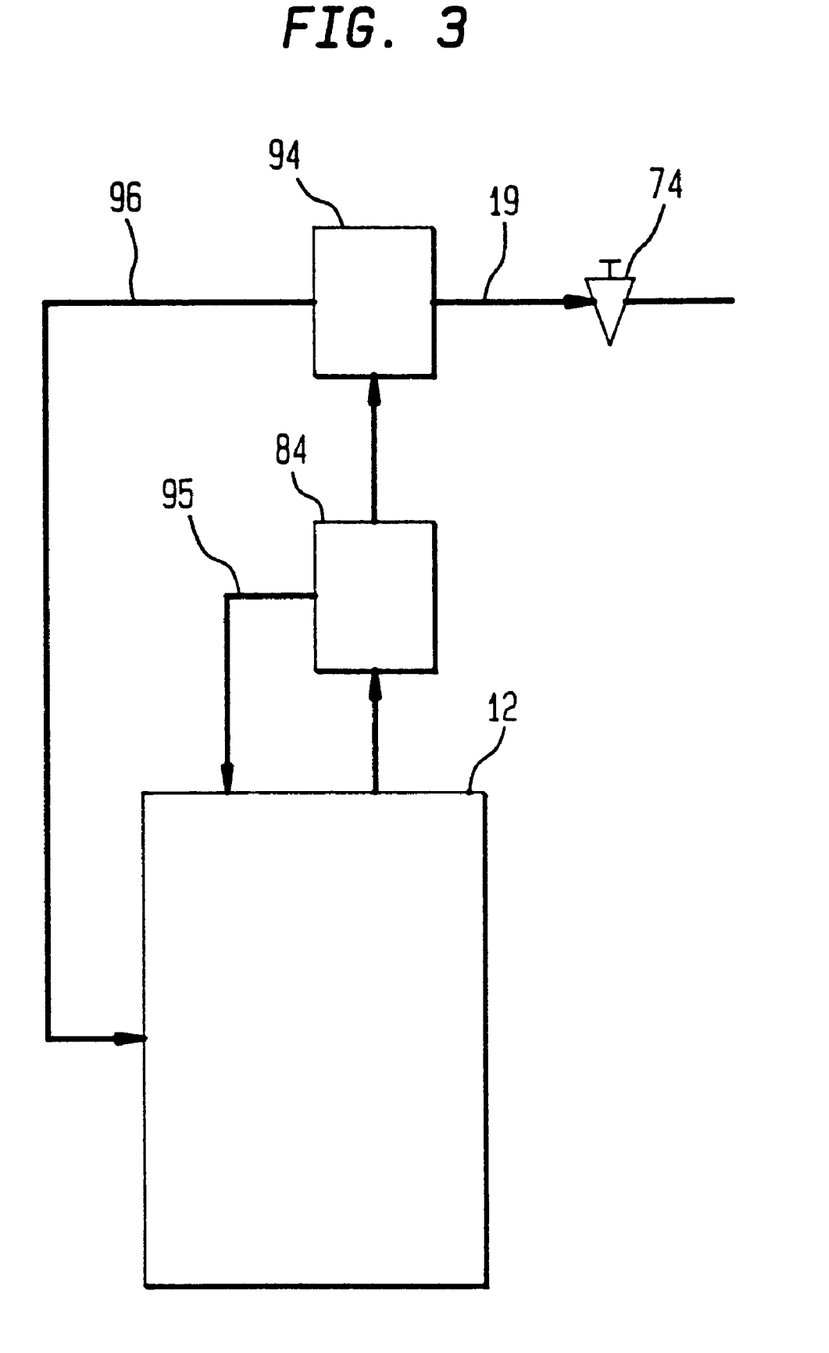
FIG. 3 illustrates another preferred arrangement showing recirculation of condensible and non-condensible gases.

It should be stressed that it is highly preferable in many occasions, especially in the case of stirred tank reactors, to introduce a splitter 94 (see FIG. 3), which splits the stream of non-condensible off-gases to two streams; one stream toward valve 74 through line 19, and one stream toward the reaction chamber 12, for recycling substantially non-condensible off-gases back to the reaction chamber 12. Vigorous recycling of non-condensible off-gases to the reaction chamber 12 for continuing sparging, even when no new gases are entering the reaction chamber 12, or leaving through valve 74, is very desirable for avoiding undue pressure changes, which are unrelated to the consumption of oxidant. Condensible off-gases return to the reaction chamber 12 through line 95 substantially as condensate. It is evident that any recycled matter has to be taken into account when oxidant consumption rate, hydrocarbon consumption rate, reaction rate, and reactivity, among other parameters are being determined.

According to another preferred embodiment of the instant invention, the difference in flow rates between the incoming and outgoing gases, after appropriate corrections, if necessary, is utilized as a fast and easy way to monitor and control the oxidant consumption rate, and in turn, be able to maintain the reaction rate or the reactivity within desirable predetermined limits.

The flow rate difference and operations involved with monitoring and or control of the reaction rate or of the reactivity may be made on a continuous basis, or a sporadic basis, or in any desirable predetermined pattern.

The reactor device shown in FIG. 1 may also be used for the practice of this embodiment.

Figure 2:
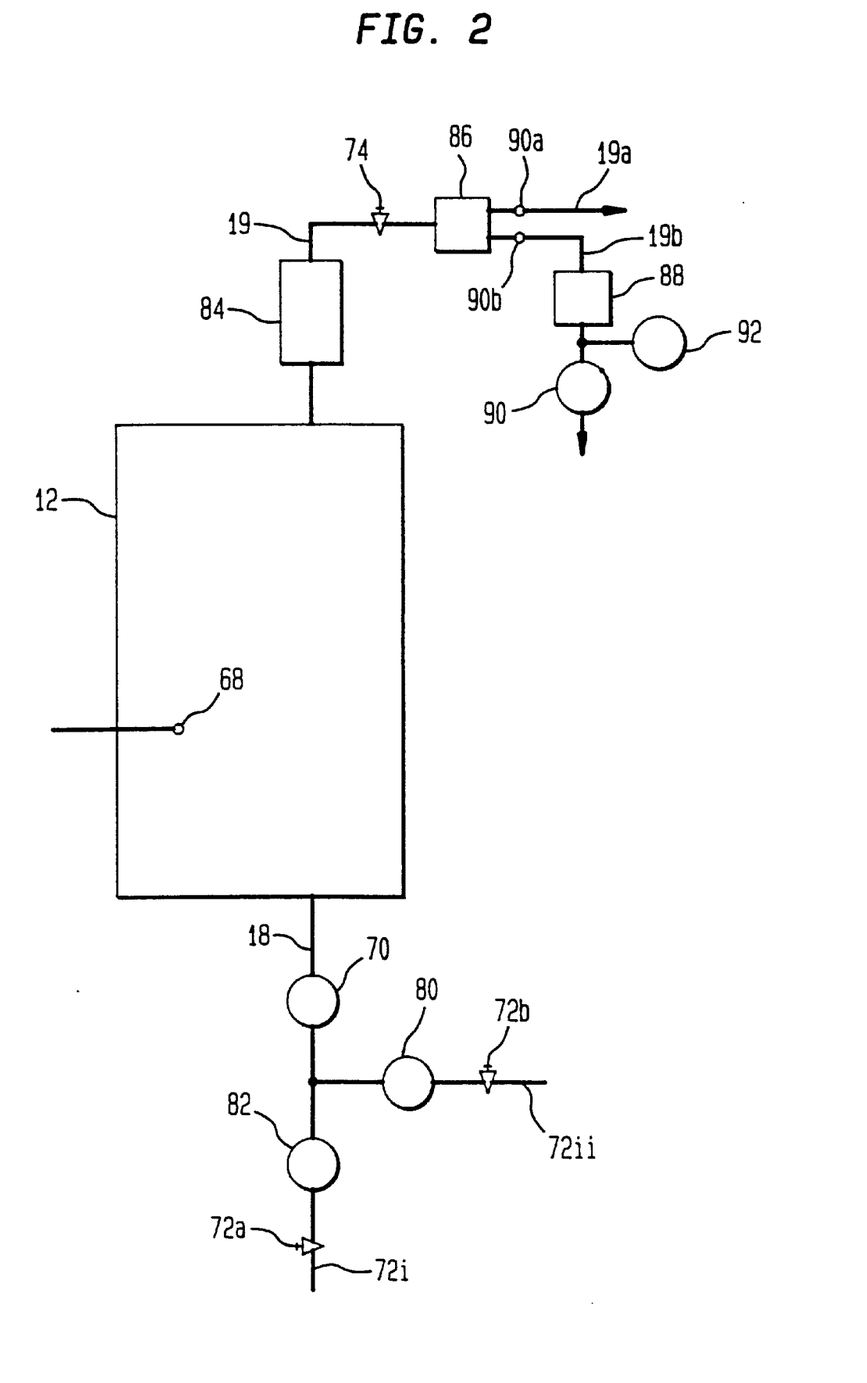
FIG. 2 illustrates in more detail a preferred arrangement of elements for measuring flow rates and oxidant rates of the outcoming gases.

It is highly preferable that a condenser (not shown in FIG. 1 for purposes of clarity) is in line 19 before the valve 74 and the flowmeter 76. It is further highly preferable that means (not shown in FIG. 1 for purposes of clarity) for bringing the temperature of at least a portion of the non-condensible off-gases to substantially the same temperature as the temperature of the incoming gases through line 18. A more detailed schematic diagram of these preferred aspects is shown in FIG. 2. In line 19, preferably between the valve 74 and the reaction chamber 12, there is disposed a condenser 84, well known to the art, for condensing miscellaneous condensible materials, so that substantially only non-condensible gases pass through valve 74, which leads to a gas divider 86. Gas dividers are well known to the art. The may have a baffle or other closing means for dividing a stream of gas into two streams. They may vary the baffle opening in a manner that the ratio of the two streams with respect to each other is variable, and adjustable either manually or preferably automatically, in a manner to achieve a constant desired ratio. The gas divider 86 leads to line 19a, carrying the major portion of the non-condensible off-gases, and line 19b carrying a minor part of the non-condensible off-gases. The flowmeters 90a and 90b are connected in lines 19a and 19b, respectively, for measuring the flows in the two lines at the same temperature, which usually is higher than ambient temperature. The two flowmeters provide flow information to the controller 28 (FIG. 1), which in turn controls the divider 86 in a manner to provide a desirable ratio of the two streams. A heat exchanger 88 is positioned between the flowmeters 90b and 90 in order to bring the temperature of the gas stream passing through line 19b to the same level as the temperature of gas entering the reaction chamber 12. Flowmeters 80 and 82 are disposed as shown in FIG. 2 for monitoring the flow rate of gaseous streams passing through lines 72ii and 72i, respectively.

Means for conducting chemical analysis of the contents of the reaction chamber 12, or any other lines, are not shown in FIG. 1, also for purposes of clarity. The means (not shown) for conducting chemical analysis, preferably, also provide ingredient content information to the controller 28. The inlet, outlet, input or output lines may be positioned in any suitable location of the reaction chamber 12.

From the flow rates provided by the flowmeters 70, 80, and 82, and from the composition of the gases passing through lines 72i and 72ii, the amount of oxidant entering the reaction chamber 12 may be easily calculated by the controller 28. From the flow rates provided by the flowmeters 90a and 90b, and from the composition of gases in line 19b, the amount of oxidant leaving the reaction chamber 12 may be easily calculated by the controller 28. The difference of the amount of oxidant coming in and of the amount of the oxidant going out of the reaction chamber 12 per unit of time, is of course a measure of the oxidant consumption rate.

During the reaction, non-condensible off-gases along with condensibles exit the reaction chamber 12 through line 19. The condensible matter is condensed in condenser 84 and returns partially or totally to the reaction chamber 12. The substantially non-condensible off-gases, pass through valve 74 and enter the gas divider 86, where they are divided into two streams. The major stream passes through flowmeter 90a and leaves the system for discarding or treatment, or other type of disposal, while the minor stream, after passing through flowmeter 90b, enters the heat exchanger 88, where it assumes substantially the same temperature as the stream passing through flowmeter 70 in line 18. Input and output lines connecting these elements to the controller 28 are not shown for purposes of clarity, but they are evident to a person of ordinary skill in the art. Of course, the divider may be omitted and flow measurements conducted in the total amount of non-condensible off-gasses. Further, the heat exchanger may be omitted, and the temperature differences between the incoming and outgoing gases taken into account for the calculations of the reaction rate or of the reactivity. It is preferable that the pressure inside the reaction chamber is constant, at least when the measurements of flow rates are taken; otherwise the calculations become more complicated.

The controller 28, based at least partially on information received from flowmeters 70, 80, 82, 90, 90a, and 90b and oxidant concentration data, calculates from the difference in flow rates between inlet line 18 and outlet line 19, after correcting for temperature and pressure differences, the amount of oxygen consumed per unit time or the oxidant consumption rate, and therefrom the reaction rate and/or the reactivity (reaction rate divided by the total volume of non-gaseous mixture involved in the reaction).

As aforementioned, deviations of the results because of formation of small amounts of gaseous products, such as carbon monoxide and carbon dioxide, are minor and may be ignored in most cases and for all practical purposes. However, monitors for their detection and measurement may be used, if so desired.

This process and device to measure the reaction rate or the reactivity is continuous and highly efficient.

As in the previous case, when the determination of the oxidant consumption rate, and of the reaction rate or of the reactivity has been made, appropriate action, as described above, may be taken to control said reaction rate or said reactivity to fall within a desired region.

In still another embodiment of the present invention, a monitor (FIG. 2) for oxygen content in line 19, may be used in a manner that the controller 28, after being fed with such information, may calculate the oxidant consumption rate, and in turn the rate of oxidation, taking also into account the amount of oxidant entering the reaction chamber 12.

Further, in another embodiment, the reaction rate may be adequately approximated solely based on oxidant concentration changes in the reaction chamber 12, or by oxidant concentration changes in the off-gas line immediately exiting the reaction chamber 12. In this case also, if the approximated reaction rate moves or is outside the desired range of the predetermined limits, the consumption rate of oxidant is changed in a manner to bring said reaction rate within the desired limits. Ways of changing the oxidant consumption rate have already been discussed earlier.

A preferable type of controller is a computerized controller. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and it is programmed to use this information in the future, along with other data if applicable, to make decisions regarding the action to be at each instance. The expert systems are programmed based on the expertise of experienced human beings. The fuzzy logic systems are based on intuition rules in addition to expertise rules.

Although the miscellaneous functions are preferably controlled by the controller 28, it is possible, according to this invention, to utilize manual controls for controlling one or more functions.

Although the results of the oxidant consumption rate and in turn of the rate of the reaction and/or reactivity are used preferably to control and maintain said rate of reaction and/or reactivity within predetermined desirable limits, it is possible to be used just as a warning signal or system to the operator, by setting off an alarm for example, or giving another indication for example that said reaction rate and/or said reactivity is outside the desirable limits, so that the operator, depending on the circumstances, may decide whether to take action or postpone action until more data are available.

Oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to
    preparation of $C_5$–$C_8$ aliphatic dibasic acids from the corresponding saturated cycloaliphatic hydrocarbons, such as for example preparation of adipic acid from cyclohexane;

preparation of $C_5$–$C_8$ aliphatic dibasic acids from the corresponding ketones, alcohols, and hydroperoxides of saturated cycloaliphatic hydrocarbons, such as for example preparation of adipic acid from cyclohexanone, cyclohexanol, and cyclohexylhydroperoxide;

preparation of $C_5$–$C_8$ cyclic ketones, alcohols, and hydroperoxides from the corresponding saturated cycloaliphatic hydrocarbons, such as for example preparation of cyclohexanone, cyclohexanol, and cyclohexylhydroperoxide from cyclohexane; and preparation of aromatic multi-acids from the corresponding multi-alkyl aromatic compounds, such as for example preparation of phthalic acid, isophthalic acid, and terephthalic acid from o-xylene, m-xylene and p-xylene, respectively.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Examples of other hydrocarbons, which may be utilized according to this invention are methylated aromatic compounds, such as for example toluene, xylenes, methylated naphthalenes, etc.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

When referring to gasses entering or leaving the reaction chamber 12, recirculating gases from line 96 (FIG. 3) are considered to be within the reaction chamber 12. The same applies for condensible gases, which are condensed in the condenser 84 and they are recirculated to the reaction chamber 12 through line 95 as condensate.

What is claimed is:

1. A method of controlling the oxidation of a hydrocarbon to an intermediate oxidation product in a reaction zone, the method characterized by the steps of:

(a) contacting a gas comprising oxidant with a hydrocarbon by feeding the gas at a first flow rate, and the hydrocarbon into the reaction zone, at a first pressure, and at a first temperature adequately high to allow the oxidant to react with the hydrocarbon at a reactivity; and (b) determining and controlling the consumption rate of the oxidant in a manner that the reactivity is maintained within or driven toward a range of predetermined limits.

2. A method as defined in claim 1 wherein the consumption rate of the oxidant is determined by the difference of oxidant entering the reaction zone and oxidant leaving the reaction zone per unit of time.

3. A method as defined in claim 1 wherein the consumption rate of the oxidant is determined by the difference of hydrocarbon entering the reaction zone and hydrocarbon leaving the reaction zone per unit of time.

4. A method as defined in claim 1 wherein the consumption rate of the gaseous oxidant is determined by a difference between the first flow rate and the flow rate of non-condensible off-gases.

5. A method as defined in claim 1, wherein the consumption rate of the oxidant is controlled by regulating a variable selected from a group consisting of temperature, pressure, partial pressure of oxidant, flow rate of oxidant, sparging rate, recycled gas flow rate, flow rate of hydrocarbon, flow rate of solvent, flow rate of catalyst, flow rate of water, flow rate of initiator or promoter, and a combination thereof.

6. A method as defined in claim 1, further comprising a step of atomization of liquids entering the reaction zone.

7. A method as defined in claim 1 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

8. A method as defined in claim 2 wherein the consumption rate of the oxidant is controlled by regulating a variable selected from a group consisting of temperature, pressure, partial pressure of oxidant, flow rate of oxidant, sparging rate, recycled gas flow rate, flow rate of hydrocarbon, flow rate of solvent, flow rate of catalyst, flow rate of water, flow rate of initiator or promoter, and a combination thereof.

9. A method as defined in claim 3 wherein the consumption rate of the oxidant is controlled by regulating a variable selected from a group consisting of temperature, pressure, partial pressure of oxidant, flow rate of oxidant, sparging rate, recycled gas flow rate, flow rate of hydrocarbon, flow rate of solvent, flow rate of catalyst, flow rate of water, flow rate of initiator or promoter, and a combination thereof.

10. A method as defined in claim 4 wherein the consumption rate of the oxidant is controlled by regulating a variable selected from a group consisting of temperature, pressure, partial pressure of oxidant, flow rate of oxidant, sparging rate, recycled gas flow rate, flow rate of hydrocarbon, flow rate of solvent, flow rate of catalyst, flow rate of water, flow rate of initiator or promoter, and a combination thereof.

11. A method as defined in claim 2, further comprising a step of atomization of liquids entering the reaction zone.

12. A method as defined in claim 3, further comprising a step of atomization of liquids entering the reaction zone.

13. A method as defined in claim 4, further comprising a step of atomization of liquids entering the reaction zone.

14. A method as defined in claim 2 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

15. A method as defined in claim 3 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

16. A method as defined in claim 4 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

17. A method as defined in claim 5 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

18. A method as defined in claim 6 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

19. A method as defined in claim 18 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

20. A method as defined in claim 9 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

21. A method as defined in claim 10 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

22. A method as defined in claim 11 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

23. A method as defined in claim 12 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

24. A method as defined in claim 13 wherein the intermediate compound comprises adipic acid, the hydrocarbon comprises cyclohexane, the solvent comprises acetic acid, the catalyst comprises a cobalt compound, and the optional initiator or promoter comprises a compound selected from a group comprising acetaldehyde, cyclohexanone, and a combination thereof.

\* \* \* \* \*